US010220061B1

(12) United States Patent
Denapoli et al.

(10) Patent No.: US 10,220,061 B1
(45) Date of Patent: Mar. 5, 2019

(54) METHOD OF REDUCING STRESS AND ANXIETY IN EQUINES

(71) Applicants: Cynthia Denapoli, Scottsdale, AZ (US); Albert Denapoli, Scottsdale, AZ (US)

(72) Inventors: Cynthia Denapoli, Scottsdale, AZ (US); Albert Denapoli, Scottsdale, AZ (US)

( * ) Notice: Subject to any disclaimer, the term of this patent is extended or adjusted under 35 U.S.C. 154(b) by 4 days.

(21) Appl. No.: 15/716,034

(22) Filed: Sep. 26, 2017

(51) Int. Cl.
*A61K 36/00* (2006.01)
*A61K 47/06* (2006.01)
*A61D 99/00* (2006.01)
*A61K 9/00* (2006.01)

(52) U.S. Cl.
CPC .............. *A61K 36/00* (2013.01); *A61K 47/06* (2013.01); *A61D 99/00* (2013.01); *A61K 9/0095* (2013.01)

(58) Field of Classification Search
CPC ...................................................... A61K 36/00
USPC ........................................................ 424/725
See application file for complete search history.

(56) References Cited

U.S. PATENT DOCUMENTS

| 6,946,150 B2 | 9/2005 | Whittle |
| 8,808,734 B2 | 8/2014 | Winnicki |
| 9,629,886 B2 | 4/2017 | Franklin et al. |
| 2002/0115725 A1 | 8/2002 | Epstein et al. |
| 2004/0127518 A1 | 7/2004 | Piomelli et al. |
| 2007/0072939 A1 | 3/2007 | Kupper |
| 2010/0273895 A1 | 10/2010 | Stinchcomb et al. |
| 2016/0143972 A1 | 5/2016 | Stebbins et al. |
| 2017/0000744 A1 | 1/2017 | Kaufman |
| 2017/0189462 A1 | 7/2017 | Franklin et al. |
| 2017/0189463 A1 | 7/2017 | Franklin et al. |

FOREIGN PATENT DOCUMENTS

| CN | 101516333 A | 8/2009 |
| CN | 106999598 A | 8/2017 |
| EP | 1361864 B9 | 8/2002 |
| WO | 2012064667 A2 | 5/2012 |
| WO | 2012144892 A1 | 10/2012 |
| WO | 2015068052 A2 | 5/2015 |
| WO | 2016027259 A1 | 2/2016 |
| WO | 2016127111 A1 | 8/2016 |
| WO | 2017098502 A1 | 6/2017 |

OTHER PUBLICATIONS

Bergamaschi, et al, Cannabidiol Reduces the Anxiety Induced by Simulated Public Speaking in Treatment-Naive Social Phobia Patients, Neuropsychopharmacology (2011) 36, 1219-1226.
Rafael De Mello Schier, et al., "Cannabidiol, a Cannabis sativa constituent, as an anxiolytic drug", Official Journal of the Brazilian Psychiatric Association, vol. 34, Supplement 1, Jun. 2012.
Pertwee, Roger G., "The Pharmacology and Therapeutic Potential of Cannabidiol", Conference: American Association or the Advancement of Science 2014 Annual Meeting, Feb. 2015.

*Primary Examiner* — Michael V Meller
(74) *Attorney, Agent, or Firm* — MG Miller Intellectual Property Law LLC

(57) ABSTRACT

A method of reducing stress and anxiety in an equine comprising administering a therapeutically effective amount of a water-based cannabinoid formulation is provided, where the formulation contains no tetrahydrocannabinol. While many cannabinoids are suitable, the formulation may contain pure cannabidiol as the primary or only cannabinoid.

1 Claim, No Drawings

METHOD OF REDUCING STRESS AND ANXIETY IN EQUINES

NOTICE OF COPYRIGHTS AND TRADE DRESS

A portion of the disclosure of this patent document contains material which is subject to copyright or trade dress protection. This patent document may show and/or describe matter that is or may become trade dress of the owner. The copyright and trade dress owner has no objection to the facsimile reproduction by anyone of the patent disclosure, as it appears in the Patent and Trademark Office patent files or records, but otherwise reserves all copyright and trade dress rights whatsoever.

CLAIM OF PRIORITY

This application does not claim priority to any patent or patent application.

FIELD OF THE EMBODIMENTS

The field of the present invention and its embodiments relate generally to a method of reducing stress and anxiety in equines. More particularly, the present disclosure relates to a method of reducing stress and anxiety in equines by administering formulations containing cannabinoids, specifically cannabidiol ("CBD") and not tetrahydrocannabinol ("THC").

BACKGROUND

Equestrianism and equestrian sport have deep roots in both American and world history. While the Kentucky Derby, the Breeder's Cup, and the Belmont Stakes are the most widely known equine events in the U.S., equestrian sport is also an Olympic event. Additionally, the sport of Polo is also popular not only in the U.S. but on a global stage. In fact, these activities are so ubiquitous that the Fédération Équestre International recognizes ten distinct disciplines within the realm of equestrianism.

What this variety shows is that equines are versatile animals that can be trained to perform in many different events, with varying rules, and under numerous conditions. However, the jockey, rider, or handler are at an extreme disadvantage when training and controlling these equines. Having a weight upwards of 500 kg and reaching speeds upwards of 65 mph, safely maneuvering these animals while optimizing their performance is challenging. Not to mention, riders find themselves 3 meters above the ground with only experience and a helmet for protection.

On top of all of the above, even in equines without any pre-existing conditions, normal maintenance activities such as clipping, shoeing, and transporting can cause elevated anxiety levels which regularly result in injuries to both the animal and the people handling or riding them. According to the British Journal of Medicine and Medical Research, the main injury mechanisms include the fall off the horse, the kick of the fallen rider by the horse and, to a lesser extent, the biting by the horse, trampling by the horse or being dragged by the reins after the fall. That same study showed that 85% of the children had fall accidents, 7% were kicked, while 65% of the adults had fall accidents and 16% were kicked.

In addition to the standard faire when working with equines, both "show" and "race" horses can act very calmly when at home, but become what is known as "underperformers" when placed in competitive situations due to stress or anxiety. The unpredictability of such powerful animals further demonstrates the urgency to maintain safety protocols for those who work in the equestrian field, as well as the needs for things to go well for when the equines are engaged in equestrianism.

While there are other animals that can be trained for specific tasks, one thing that sets equines apart from other animals is the fact that they are prey animals. As such, in most situations, equines react differently than canines, felines, and most other domesticated animals. For example, when equines are placed in stressful or anxiety causing situations, often they can act in frenetic, if not violent manners, and can become a danger to themselves and those around them.

In short, equines can be very dangerous to work with, but very rewarding to do so successfully. As such, there are many new safety steps that need to be taken via pharmaceutical preparation to benefit the health of all parties involved in the sport.

Unsurprisingly, owners, jockeys, and riders often resort to extreme measures to control their equines to improve performance. This has resulted in hundreds of various compounds being either banned or controlled for use in equestrian sport. While there are many banned compounds, suppressing levels of stress and anxiety in equines will generate more efficient performance results without increasing the risk of injuries for riders and handlers. Thus, a new pharmaceutical preparation that is not on the banned substance list but can also increase the performance while maintaining the safety of the equines and riders would greatly benefit and improve the sports and events under which they are performing.

In the present disclosure, where a document, act, or item of knowledge is referred to or discussed, this reference or discussion is not an admission that the document, act, or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

SUMMARY

An aspect of an example embodiment in the present disclosure is to provide a method of reducing stress and anxiety in an equine. Accordingly, the present disclosure provides for a method of reducing stress and anxiety in an equine comprising administering a therapeutically effective amount of a water-based cannabinoid formulation. Preferably, the water-based cannabinoid formulation is a water-based cannabidiol formulation. While the formulations in accordance with the present disclosure can be absorbed in a number of ways, preferably it is absorbed through the mucous membrane of the equine. To achieve this result, the cannabinoid formulation is best administered orally, and preferably sublingually.

It is well known that both show and race horses are rigorously drug tested and that tetrahydrocannabinol, commonly referred to as "THC" is a substance banned in all equine competitions, including those governed by the United States Equestrian Federation. As such, an important aspect of the formulation of the present disclosure is that is it completely free of THC. Preferably, the primary cannabinoid in the formulation is cannabidiol, or "CBD."

As administering medicaments to equines can be very challenging, it is preferably to administer the formulation of the present disclosure via an oral syringe, and more preferably a single dose is contained in said syringe. In a preferred embodiment, the formulation has a volume in the range of 4 milliliters to 6 milliliters. In various embodiments, the water-based cannabinoid formulation contains cannabidiol in amounts in the range of 30 milligrams to 300 milligrams.

While the water-based cannabinoid formulation of the present invention can be administered on an as-needed basis, it can also be administered as part of a daily regimen. When the formulation is administered as part of a daily regiment, the preferred cannabinoid is cannabidiol and the preferred amount is 15-60 milligrams of cannabidiol per daily dose, depending on the weight of the equine.

It should be noted that many embodiments of the water-based cannabinoid formulation of the present disclosure are suitable for reducing stress, anxiety, inflammation, ADD, and PTSD in an equine, as well as for increasing focus in said equine, unlike solutions that exist in the art today.

The present disclosure addresses at least one of the foregoing disadvantages found in the prior art. However, it is contemplated that the present disclosure may prove useful in addressing other problems and deficiencies in a number of technical areas. Therefore, the claims should not necessarily be construed as limited to addressing any of the particular problems or deficiencies discussed hereinabove. Variations are contemplated as being part of the disclosure.

Implementations may include one or a combination of any two or more of the aforementioned features.

These and other aspects, features, implementations, and advantages can be expressed as methods, apparatuses, systems, components, program products, business methods, and means or steps for performing functions, or some combination thereof.

Other features, aspects, implementations, and advantages will become apparent from the descriptions and the claims.

DETAILED DESCRIPTION OF THE PREFERRED EMBODIMENTS

The present disclosure provides for a method of reducing stress and anxiety in an equine. Administering a formulation in accordance with the present disclosure is also suitable to reduce inflammation, attention deficit disorder (ADD), and post-traumatic stress disorder (PTSD) in an equine.

Formulations in accordance with the present invention include at least one cannabinoid that is not THC suspended in water. Preferably this cannabinoid is cannabidiol. As cannabinoids are not ordinarily soluble in water, they must be made into a complex with nanoparticles to achieve water-solubility. These complexes have the additional benefit of increased bioavailability and in turn, increased absorption rates. While it is possible to create these complexes, pre-formed complexes are also commercially available. One such complex is the NEC Key Concentrate sold be Hygia Nutrients, LTD, located in Watford, United Kingdom.

While these complexes are available, achieving the proper dose of cannabinoid in equines is challenging, and is disclosed herein as the product of considerable research. For non-water-soluble formulations containing cannabinoids, bioavailability is very low, and in order to achieve proper dosing and volume in equines is difficult, if not impossible. As such, the water-soluble cannabinoid formulations are required for the method of the present disclosure to be effective.

Appropriate dosage for the equine is determined by their size. As a non-limiting example where the equine is a horse, three weights classes become preferable. For example, a pony or yearling receives a dose of the formulation containing 50-100 mg of at least one cannabinoid; light horse breeds receive a dose of the formulation containing 100-200 mg of at least one cannabinoid; and warmblood breeds receives a dose of the formulation containing 150-300 mg of at least one cannabinoid. Preferably, the at least one cannabinoid is a single cannabinoid, and that single cannabinoid is cannabidiol. Further, it is also important that none of the formulations in accordance with the present invention contain even trace amounts of THC, as having THC in the formulations would make them unsuitable for use with competition equines.

As those who regularly deal with equines know, it can be challenging to administer large volumes of medicines. As such, the total volume of said dose is another important feature of the present invention. The method of delivery is also an important feature. Regarding the method of delivery, experimentation determined that a nasal spray was not suitable as the equines universally had a negative response to that form of administration. However, further research indicated that administering the formulation orally (sublingually) would be acceptable, however the use of syringes were greatly preferred as opposed to traditional droppers. Syringes offered the benefit of being able to house a single dose in a vessel that could easily be slid into the equine's mouth.

As the syringe was determined to be the most effective vessel for administering the formulations in accordance with the present disclosure, the acceptable volumes and concentrations of the formulations were determined. In a highly preferred embodiment, a single dose of the formulations in accordance with the present disclosure is in the range of 4 mL to 6 mL. In other embodiments, formulations in accordance with the present invention have concentrations of cannabinoids present in the range of 8.3 mg/mL to 75 mg/mL. This range of concentrations allows for single doses of the formulations to be effective on animals the size of standard equines, as well as be in a small enough volume to be administered easily.

While the rate of absorption varies based on a given equine's physiology as well as environmental factors, typically an equine will begin to exhibit more calm behavior approximately one-to-two hours after a dose of the formulation in accordance with the present disclosure when administered. Specifically, an equine will be easier to control, exhibit less stress and anxiety, and be more consistent in their performance after said formulation has been administered.

Example 1

The test subject is an 8-year-old Arabian Gelding. The test subject was recovering from surgery and had to be ridden slowly and quietly in order for the subject to heal from the surgery properly. The subject was reported to be " . . . wound up and almost unmanageable." The subject was given a dose of the formulation containing 100 mg of CBD. After administration of the formulation, the subject's behavior was greatly improved, and it was then possible to ride the subject in a way that allowed it to heal properly.

Example 2

The test subject is a 9-year-old Arabian Gelding. The subject was reported to suffer from sever separation anxiety. This anxiety manifested when the horses from neighboring stalls were removed and the subject would kick the stall, whirl around, and would begin hysterically calling for the other horses. The subject was given a dose of the formulation containing 100 mg of CBD. One hour after administration the test subject ceased all kicking, whirling, and calling. The subject then ate lunch and calmly stared out the door, in sharp contrast to prior behavior.

Example 3

The test subject is a 6-year-old half-Arabian mare. The test subject was very difficult to transport, even over short distances such as 5 miles. At the end of such a trip the subject would be soaking wet from sweat from being nervous, and it would take at least 30 minutes for the subject to calm down enough to be given food or water. This subject was also given a dose of the formulation that contained 100 mg of CBD 90 minutes before an attempt to transport said subject was made along that same 5-mile distance. Upon arrival, the subject was dry, cool, calm, and was able to be placed immediately in a stall. Roughly one month later the same subject was given a dose of the formulation containing 100 mg of CBD an hour before being transported 100 miles. At the end of the 100-mile trip the subject arrived dry and calm.

Example 4

The test subject is a 4-year-old Arabian mare. The subject was reported as being nervous and very difficult to train. Specifically, over an hour of lunging was required before anyone was able to ride the subject, and required an additional 15 minutes after that before the subject was settled down enough to learn new tasks. The subject was given a dose of the formulation containing 100 mg of CBD an hour before working. The subject only had to be lunged a short amount of time, and was paying attention right away. In sum, it meaningfully decreased the amount of time the subject had to be worked before the subject was able to learn.

Example 5

The test subject was a 7-year-old half-Arabian mare. The owner of the subject had attempted to show the subject for over a year and had consistently bad results. While the subject was "pretty good" at home, upon arriving at a show the subject would get very jumpy and would be challenging to walk and switch leads. The subject was given a dose of the formulation containing 50 mg of CBD and showed dramatically improved behavior. At a later date, the subject was given a dose of the formulation containing 100 mg of CBD and won the competition she was competing in; a first for the subject due to prior behavioral issues.

Example 6

The test subject was a 1-year-old Arabian colt. The subject had to be tranquilized even to do minor clipping, trimming of feet, and other grooming. The subject stood on its hind legs whenever it was removed from the stall. An hour after given a dose of the formulation containing 50 mg of CBD, the subject came out of the stall in a calm state, and did not rear or jump. The subject then allowed himself to be clipped while the subject stood calmly. After being groomed the subject was taken outside and lunged and appeared to be "bright and cheerful, not the least bit tranquilized looking or acting."

Example 7

The test subject was a 5-year-old Arabian mare. The subject was extremely traumatized due to poor prior training. In order to be ridden, the subject needed to be tranquilized. The subject was given a dose of the formulation containing 100 mg of CBD one day, and was given two doses of the formulation containing 100 mg of CBD the following day and was "a different animal to ride, she was easily manageable and was visibly relaxed." Further, the subject was reported to be performing consistently, and was calm in her stall. The next time the subject was shown, she won her class by unanimous decision.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer and/or section from another element, component, region, layer and/or section. Thus, a "first element," "component," "region," "layer" and/or "section" discussed below could be termed a second element, component, region, layer and/or section without departing from the teachings herein.

Features illustrated or described as part of one embodiment can be used with another embodiment and such variations come within the scope of the appended claims and their equivalents.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As the invention has been described in connection with what is presently considered to be the most practical and various embodiments, it is to be understood that the invention is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose the invention, including the best mode, and also to enable any person skilled in the art to practice the invention, including making and using any devices or systems and performing any incorporated methods. The patentable scope of the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

In conclusion, herein is presented a method for reducing stress and anxiety in an equine. The disclosure is illustrated by example in the drawing figures, and throughout the written description. It should be understood that numerous variations are possible, while adhering to the inventive concept. Such variations are contemplated as being a part of the present disclosure.

What is claimed is:

1. A method of treating behavioral issues caused by a competitive situation in an equine in need thereof consisting essentially of administering a therapeutically effective amount of a cannabinoid formulation which contains cannabidiol but which is free of THC, to the equine in need thereof to effectively treat the behavioral issues in the equine in need thereof, wherein the method is administered via an oral syringe.

* * * * *